(12) United States Patent
Dunkan et al.

(10) Patent No.: US 9,414,810 B2
(45) Date of Patent: Aug. 16, 2016

(54) ULTRASOUND IMAGING SYSTEM

(71) Applicant: B-K MEDICAL APS, Herlev (DK)

(72) Inventors: Kaj Dunkan, Stenlille (DK); Peter Ulrik Kann, Farum (DK); Torben Svanberg Nielsen, Copenhagen S (DK); Steen Madsen, Frederiksberg (DK); Alex Köneke, Hedehusene (DK); Jacob Enemark, Espergærde (DK)

(73) Assignee: B-K Medical Aps, Herlev (DK)

( * ) Notice: Subject to any disclaimer, the term of this patent is extended or adjusted under 35 U.S.C. 154(b) by 428 days.

(21) Appl. No.: 13/748,653

(22) Filed: Jan. 24, 2013

(65) Prior Publication Data

US 2014/0204699 A1 Jul. 24, 2014

(51) Int. Cl.
*A61B 8/00* (2006.01)
*G01S 15/89* (2006.01)
*G01S 15/00* (2006.01)

(52) U.S. Cl.
CPC ............... *A61B 8/467* (2013.01); *A61B 8/4438* (2013.01); *A61B 8/465* (2013.01); *G01S 15/89* (2013.01)

(58) Field of Classification Search
USPC .......................................................... 367/11
See application file for complete search history.

(56) References Cited

U.S. PATENT DOCUMENTS

| | | | | |
|---|---|---|---|---|
| 8,517,946 B2* | 8/2013 | Kim | ........................ | A61B 8/00 345/649 |
| 9,119,586 B2* | 9/2015 | Jensen | ................. | A61B 8/4405 |
| 2005/0030629 A1* | 2/2005 | Kursawe et al. | .............. | 359/586 |
| 2007/0273973 A1* | 11/2007 | Kursawe et al. | .............. | 359/584 |
| 2008/0284958 A1* | 11/2008 | Hiroya | .............. | G02F 1/133528 349/123 |
| 2009/0012401 A1* | 1/2009 | Steinbacher | ................... | 600/459 |
| 2009/0247874 A1* | 10/2009 | Kim | ......................... | A61B 8/00 600/443 |
| 2010/0145195 A1* | 6/2010 | Hyun | ............................. | 600/437 |
| 2011/0257561 A1* | 10/2011 | Gertner et al. | .................... | 601/2 |
| 2012/0038857 A1* | 2/2012 | Hiroya | .................. | G02F 1/1337 349/96 |
| 2012/0282479 A1* | 11/2012 | Everaerts | ................ | B32B 27/00 428/522 |
| 2012/0289828 A1* | 11/2012 | Jensen | ................. | A61B 8/4405 600/437 |
| 2013/0168532 A1* | 7/2013 | Schmid et al. | ................. | 250/205 |
| 2013/0253323 A1* | 9/2013 | Kim | ......................... | A61B 8/00 600/443 |
| 2013/0303875 A1* | 11/2013 | Joy et al. | ........................ | 600/407 |
| 2013/0336551 A1* | 12/2013 | Clingman et al. | ............ | 382/128 |

* cited by examiner

*Primary Examiner* — James Hulka

(74) *Attorney, Agent, or Firm* — Anthony M. Del Zoppo, III; Driggs, Hogg, Daugherty & Del Zoppo, Co. LPA

(57) ABSTRACT

An ultrasound imaging system includes a probe with a transducer array with at least one transducer element that transmits ultrasound signal and receives echo signals produced in response thereto. The system further includes a console with a controller that controls the at least one element to transmit the ultrasound signals and receive the echo signals, and an echo processor that processes the received echoes and generates images indicative thereof. The system further includes a user interface with at least one control for interacting with the console. The user interface includes at least one recessed physical feature that facilitates identifying, through sense of touch, an operation activated by the at least one control.

20 Claims, 5 Drawing Sheets

ULTRASOUND IMAGING SYSTEM

TECHNICAL FIELD

The following generally relates to an ultrasound imaging system.

BACKGROUND

An ultrasound (US) imaging system has included an ultrasound probe with a transducer, a console with an internal or external display, and a keyboard. The transducer transmits an ultrasound signal into a field of view and receives echoes produced in response to the signal interacting with structure therein. The echoes are processed by the console, which generates images indicative of the structure that are visually presented in the display region.

An example of a suitable display region includes a screen (e.g., LCD, CRT, etc.) with a cover lens (e.g. made of glass). The cover lens provides a surface that is relatively easy to clean. Shattering of the cover lens can be mitigated through a bonding material applied between the cover lens and the screen. However, the cover lens adds at least two surface transitions, an air to cover lens transition and a cover lens to air transition. Unfortunately, both the air to cover lens transition and the cover lens to air transition produce reflections, which may deteriorate the optical perception of the visually presented image. Furthermore, the distance between the touch screen display and the cover lens may result in a parallax that decreases the accuracy of activation of the individual buttons on the touch screen display.

An example of a suitable keyboard includes a keyboard with a coherent, flat surface, without any holes, for example, a "touch screen" display with a cover lens. Unfortunately, the distance between the cover lens and the screen may deteriorate the optical perception of the visually presented image and may result in a parallax that decreases the accuracy of activation of the individual buttons on the "touch screen" display. Likewise, the cover lens provides a surface that is relatively easy to clean. Unfortunately, with such a keyboard, it may not be easy for a clinician to navigate an image while observing the image without looking away from the image in the display region and looking at the keyboard to locate and activate touch screen controls.

SUMMARY

Aspects of the application address the above matters, and others.

In one aspect, an ultrasound imaging system includes a probe with a transducer array with at least one transducer element that transmits ultrasound signal and receives echo signals produced in response thereto. The system further includes a console with a controller that controls the at least one element to transmit the ultrasound signals and receive the echo signals and an echo processor that processes the received echoes and generates images indicative thereof. The system further includes a user interface with at least one control for interacting with the console. The user interface includes at least one recessed physical feature that facilitates identifying, through sense of touch, an operation activated by the at least one control.

In another aspect, an ultrasound imaging system includes a probe with a transducer array with at least one transducer element that transmits ultrasound signal and receives echo signals produced in response thereto. The system further includes a console with a controller that controls the at least one element to transmit the ultrasound signals and receive the echo signals and an echo processor that processes the received echoes and generates images indicative thereof. The system further includes a display region with a screen, a cover lens and an optical coupling there between. A refractive index of the optical coupling is approximately the same of a refractive index of the cover lens and a refractive index of the screen.

In another aspect, a method includes providing an ultrasound console, interfacing a user interface with the ultrasound console, interfacing a display region with the ultrasound console and interfacing a transducer probe with the ultrasound console, and using the transducer probe to scan an object or subject under control of the console, wherein an operator of the system controls at least one operation via the user interface and generated images are displayed via the display region. The user interface includes at least one control for interacting with the console, wherein the user interface includes at least one recessed physical feature that facilitates identifying, through sense of touch, an operation activated by the at least one control, and the display region includes a screen, a cover lens and an optical coupling there between, wherein a refractive index of the optical coupling is approximately the same of a refractive index of the cover lens and a refractive index of the screen.

Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which.

DETAILED DESCRIPTION

Figure 1:
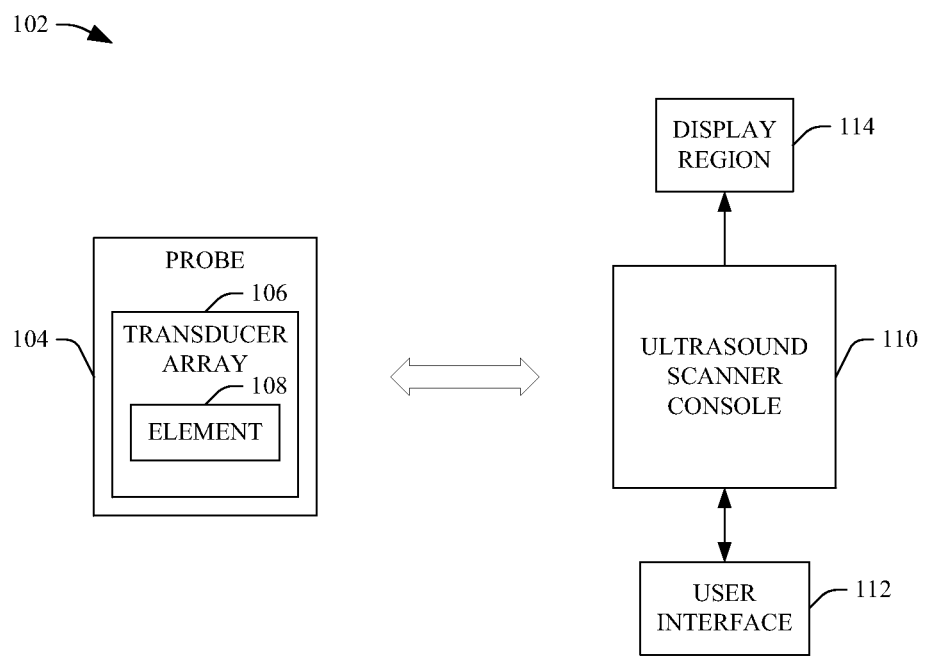
FIG. 1 schematically illustrates an example imaging system, including a user interface and a display region.

FIG. 1 schematically illustrates an ultrasound (US) imaging system 102.

The system 102 includes a probe 104 with a one-dimensional (1D) or two-dimensional (2D) transducer array 106 with at least one transducer element 108. Suitable configurations include, but are not limited to, linear, curved (e.g., concave, convex, etc.), circular, etc.

The system 102 includes an ultrasound scanner console 110 that controls excitation of the probe 104, receives and processes ultrasound data from the probe 104, and generates images to display.

The system 102 includes a user interface 112 with at least one control for interacting with the console 110. As described in greater detail below, in one non-limiting instance, the user interface 122 includes at least one recessed physical feature that facilitates identifying, through sense of touch (or haptics), an operation activated by the at least one control.

The system 102 includes at least one display region 114 that displays images generated by the console 110. As described in greater detail below, in one non-limiting instance, the display region 124 includes a screen with a cover lens optically bonded thereto, which may improve image quality relative to a configuration in which the optical bonding is omitted.

Figure 2:
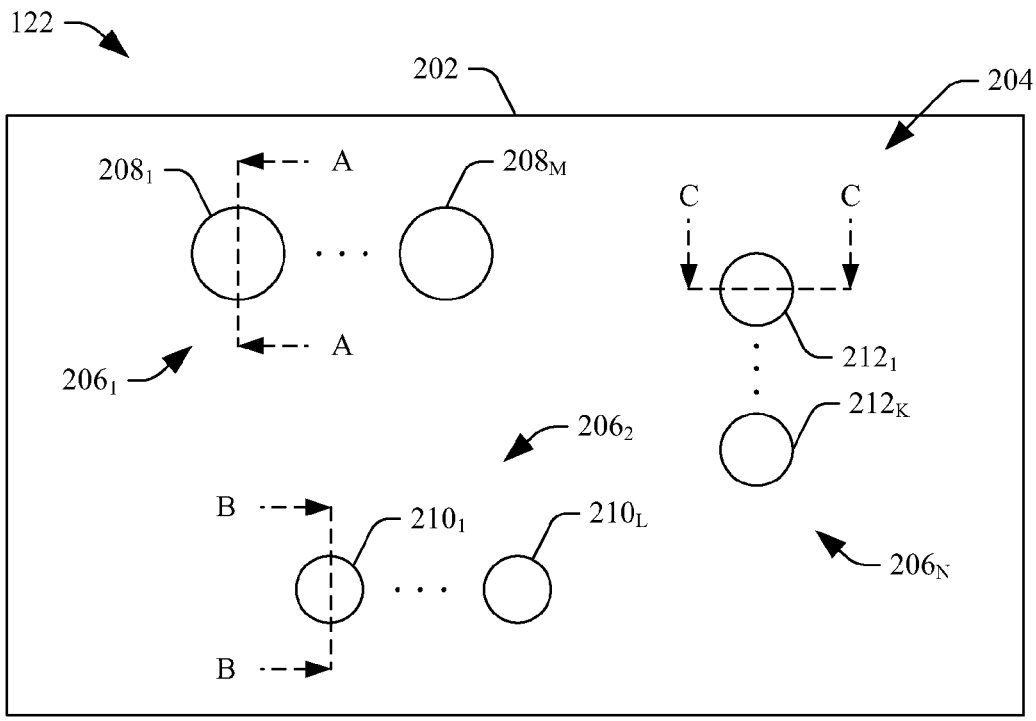
FIG. 2 illustrates an example of the user interface, which includes at least one control of FIG. 1.

FIG. 2 illustrates a top down view looking into an example of the user interface 122.

The illustrated user interface 122 includes a flat touch panel 202, in which predetermined regions thereof evoke actions in response to being actuated by simple or multi-touch gestures of the screen with one or more fingers, a stylus, a glove, etc. Suitable touchscreen panels includes, but are not limited to, resistive, projected capacitive, surface acoustic wave, infrared, optical, or piezoelectric.

The touchscreen can be, but is not limited to, a screen (e.g., liquid crystal display (LCD), thin film transistor liquid crystal display (TFT LCD), organic light-emitting diode (OLED) etc.) with a cover lens (e.g. made of glass) optically bonded thereto, which may mitigate parallax relative to a configuration in which the optical bonding is omitted.

The illustrated touch panel 202 further includes a plurality of touch sensitive controls 204. In the illustrated example, the touch sensitive controls 204 include N sets of controls $206_1$, $206_2$, ..., $206_N$, collectively referred to herein as sets of controls 206, where N is an integer equal to or greater than one.

The first set of controls $206_1$ includes M controls $208_1$, ..., $208_M$, (collectively referred to as controls 208), where M is an integer equal to or greater than one. The second set of controls $206_2$ includes L controls $210_1$, ..., $210_L$, (collectively referred to as controls 210), where L is an integer equal to or greater than one. The third set of controls $206_N$ includes K controls $212_1$, ..., $212_K$, (collectively referred to as controls 212), where K is an integer equal to or greater than one.

As described herein, the user interface 122 includes at least one recessed physical feature that facilitates identifying, through sense of touch, an operation activated by the N sets of controls $206_1$, $206_2$, ..., $206_N$. With respect to FIG. 2, the user interface 122 includes a recessed physical feature in connection with each of the of touch sensitive controls 204. This is shown in greater detail in FIGS. 3, 4 and 5 respectively in connection with the N sets of controls $206_1$, $206_2$, ..., $206_N$.

Figure 3:
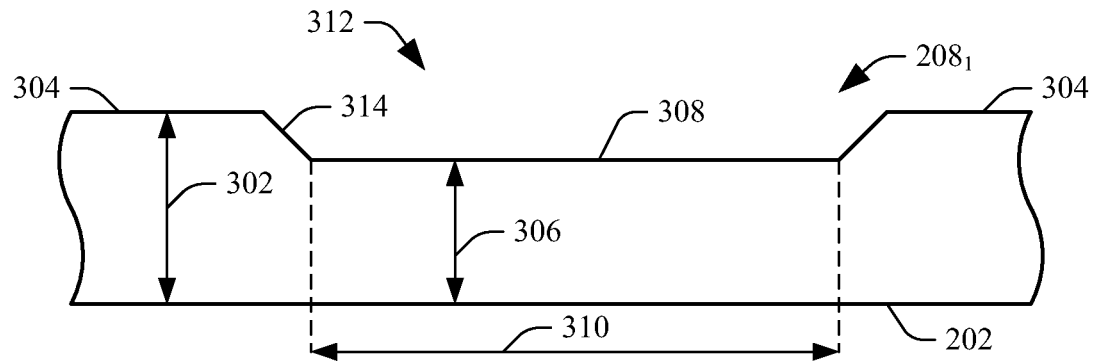
FIG. 3 illustrates an example of a first recessed control of the user interface of FIG. 2.

Initially referring to FIG. 3, a cross sectional view of the touch panel 202 and the control $208_1$ along line A-A of FIG. 2 is illustrated.

The touch panel 202 has a thickness 302 and a major surface 304. The control $208_1$ has a thickness 306 (which is less than the thickness 302 of the touch panel 202), a flat recess surface 308 and a diameter 310, and is located in a recess 312 in the major surface 304. A transition surface 314 extends from the major surface 304 into the touch panel 202 to the flat recess surface 308, forming the recess 312.

With the configuration of FIG. 3, the at least one recessed physical feature includes the transition surface 314 and the flat recess surface 308. The transition surface 314 and the flat recess surface 308 facilitate identifying a location of the control $208_1$ and the flat recess surface 308 identifies the control $208_1$. For example, in the illustrated embodiment, the transition surface 314 and the flat recess surface 308 facilitates identifying the control $208_1$ as a touch pad area. As discussed herein, the touch pad area can be used to control a cursor displayed in the display region 124, for example, cursor movement.

Figure 4:
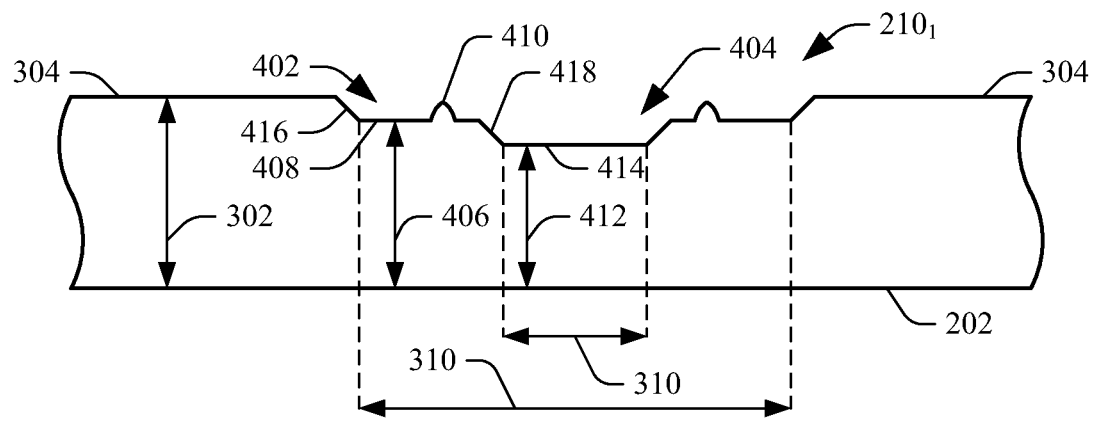
FIG. 4 illustrates an example of a second recessed control of the user interface of FIG. 2.

Turning to FIG. 4, a cross sectional view of the touch panel 202 and the control $210_1$ along line B-B of FIG. 2 is illustrated. Again, the touch panel 202 has the thickness 302 and the major surface 304.

The control $210_1$ includes a first recess 402, which is located in the major surface 304, and a second recess 404, which is located in the first recess 402. The first recess 402 has a first thickness 406 (which is less than the thickness 302 of the touch panel 202), a first recess surface 408, and a first protrusion 410. The second recess 404 has a second thickness 412 (which is less than the first thickness 406 of the first recess 402) and a second recess surface 414.

A first transition 416 extends from the major surface 304 into the touch panel 202 to the first recess surface 408, forming the first recess 402. The protrusion 410 is located in the first recess 402, spaced apart from the first transition surfaces 416 by a non-zero distance. A second transition surface 418 extends from the first recess 402 further into the touch panel 202 to the second recess surface 414, forming the second recess 404.

With the configuration of FIG. 4, the at least one recessed physical feature includes the first transition 416 and the protrusion 410, which facilitate identifying a location of a first sub-control of the control $210_1$ and, in particular, a rotary or other control, which is located in the first recess 402, between the first transition 416 and the protrusion 410. The rotary control is actuated by sliding an object on the first recess surface 408.

The at least one recessed physical feature further includes the second transition 418, which facilitates identifying a location of a second sub-control of the control $210_1$ and, in particular, a push button or other control, which is located in the second recess 404, within the second transition 418. The push button control is actuated by pushing down on the second recess surface 414.

The illustrated control $210_1$ is a multi-function control. The illustrated control $210_1$ includes two sub-controls; however, in another embodiment, the control $210_1$ includes more than two sub-controls.

Figure 5:
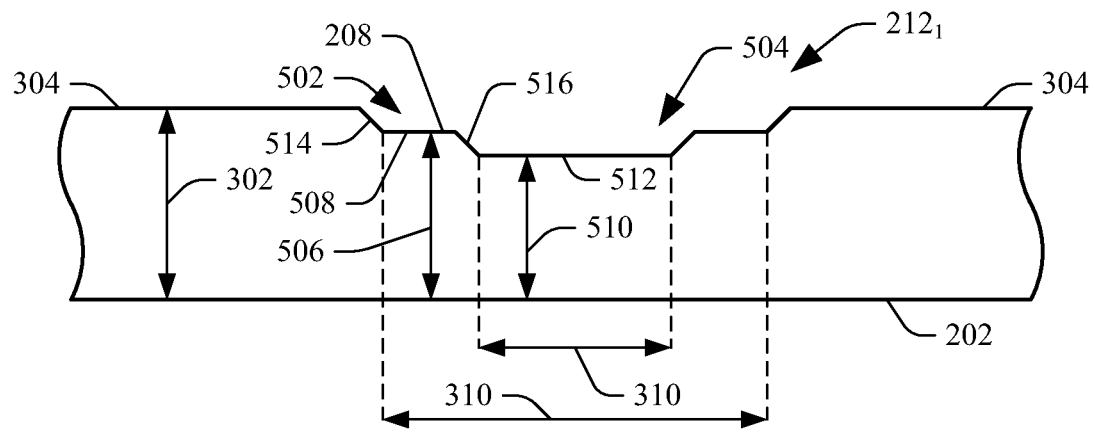
FIG. 5 illustrates an example of a third recessed control of the user interface of FIG. 2.

Next at FIG. 5, a cross sectional view of the touch panel 202 and the control $212_1$ along line C-C of FIG. 2 is illustrated. Again, the touch panel 202 has the thickness 302 and the major surface 304.

The control $212_1$ includes a first recess 502, which is located in the major surface 304, and a second recess 504, which is located in the first recess 502. The first recess 502 has a first thickness 506 (which is less than the thickness 302 of the touch panel 202) and a first recess surface 508, and the second recess 504 has a second thickness 510 (which is less than the first thickness 506 of the first recess 502) and a second recess surface 512.

A first transition 514s extend from the major surface 304 into the touch panel 202 to the first recess surface 508, forming the first recess 502. A second transition surface 516 extends from the first recess 502 further into the touch panel 202 to the second recess surface 512, forming the second recess 504.

With the configuration of FIG. 5, the at least one recessed physical feature includes the first transition 514, the first recess surface 508, the second transition 516, and the second recess surface 512 of the second recess 504, which facilitate identifying a location of the control $212_1$ and, in particular, a push button or other control, which is located in the second recess 504, within the second transition 516. The push button control is actuated by pushing down on the second recess surface 512.

Figure 6:
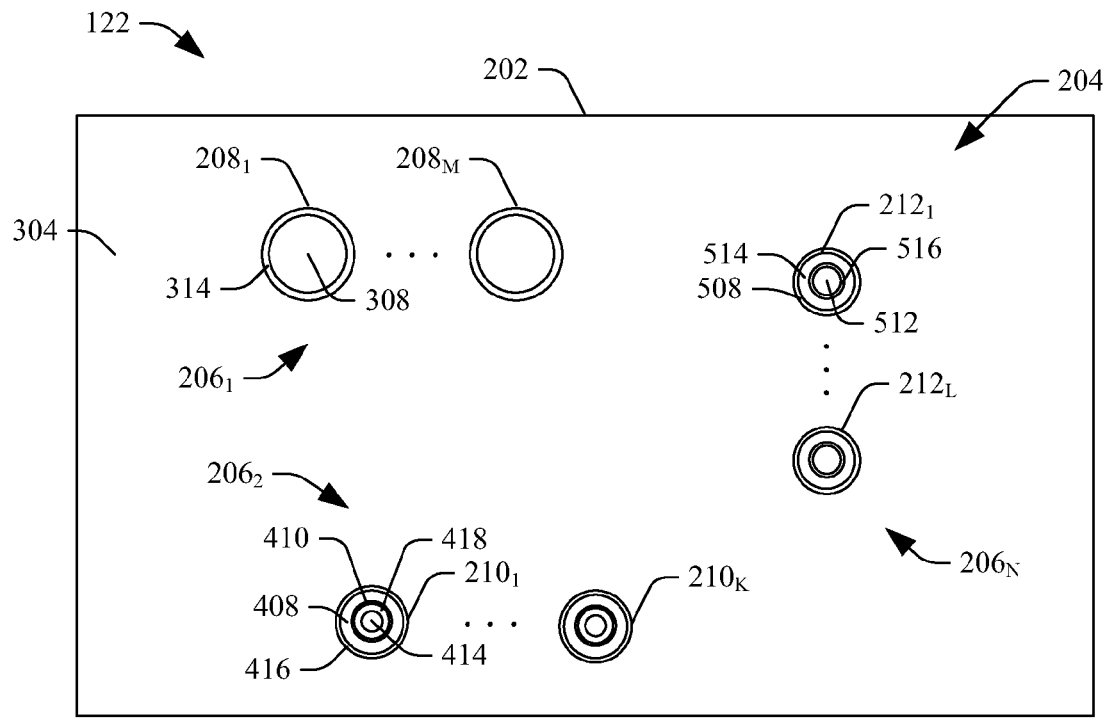
FIG. 6 illustrates the user interface of FIG. 2, with the controls of FIGS. 3, 4 and 5.

FIG. 6 illustrates the top down view of FIG. 2, in which the N sets of controls $206_1$, $206_2$, . . . , $206_N$ are configured as discussed in connection with FIGS. 3, 4 and 5. However, it is to be appreciated that the sets of controls $206_1$, $206_2$, . . . , $206_N$ can include more or less controls and/or similar or different controls. Furthermore, the illustrated geometry of the controls in non-limiting. For example, other shapes (e.g., elliptical, rectangular, etc.) and/or relative sizes are contemplated herein.

Moreover, the N sets of controls $206_1$, $206_2$, . . . , $206_N$ may include textured surfaces. For example, the rotary or other control of the sets of controls $206_2$ may include roughness, which facilitates sliding a finger along the surface and mitigating having the finger stick to the surface. Likewise, one of more of the other sets of controls $206_1$, $206_2$, . . . , $206_N$ may or may not have roughness.

Figure 7:
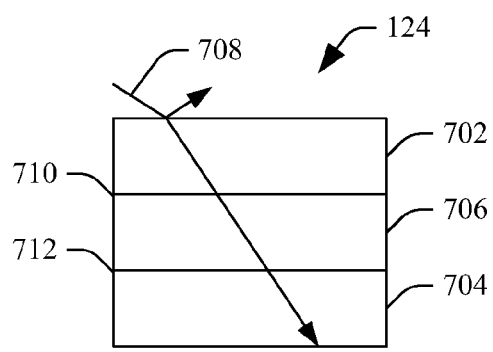
FIG. 7 illustrates an example of the display region of FIG. 1 with a cover lens optically bonded to a screen and external light traversing the display region.
Figure 8:
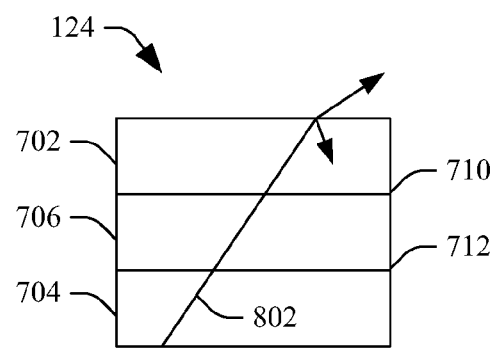
FIG. 8 illustrates an example of the display region of FIG. 1 with a cover lens optically bonded to a screen with light emitted by the screen and traversing the display region.

FIGS. 7 and 8 illustrate an example of the display region 114 of the console 110 and/or an example of the user interface 112.

The display region 114 includes a screen 704 with a cover lens 702. The screen 704 and the cover lens 702 are coupled via an optical coupling 706. The optical coupling 706 has a refractive index that substantially matches a refractive index of the screen 704 and the cover lens 702. For example, wherein the refractive index of the screen 704 is approximately 1.5 and the refractive index of the cover lens 702 is approximately 1.5, a suitable refractive index of the optical coupling 706 is 1.5.

The screen 704 can be a LCD, a TFT-LCD, an OLED, and/or other screen. The material 706 can be a liquid, a gas, a gel, a glue (e.g., silicon or other), a laminate, a plastic, a foil, and/or other optical coupling with suitable optical properties, that is, for matching the refractive index of the screen 704 and/or cover lens 702.

As shown in FIG. 7, external light 708 traverses the cover lens 702/optical coupling 706 interface 710 and the optical coupling 706/the screen 704 interface 712 with no or substantially little reflection. As shown in FIG. 8, emitted light 802 from the screen 704 traverses the screen 704/the optical coupling 706 interface 712 and the optical coupling 706/the cover lens 702 interface 710 with no or substantially little reflection.

As a result, features visually displayed on the screen 704 and under the cover lens 702 are seen by the user on the cover lens 702 over the actual location of the features visually displayed on the screen 704. This is in contrast to a configuration in which the optical coupling 706 is omitted and air resides between the screen 704 and the cover lens 702, where the features seen by the user on the cover lens 702 are shifted (parallax) from the actual location of the features visually displayed on the screen 704.

Figure 9:
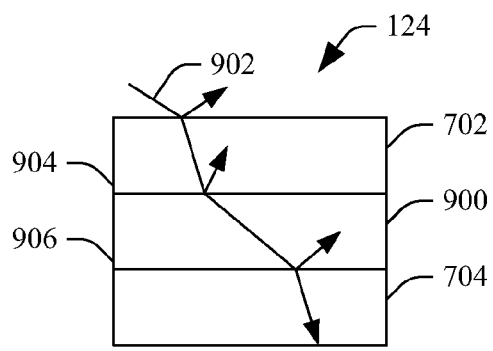
FIG. 9 illustrates a variation of the display region of FIG. 7 with the optical bond omitted therefrom.
Figure 10:
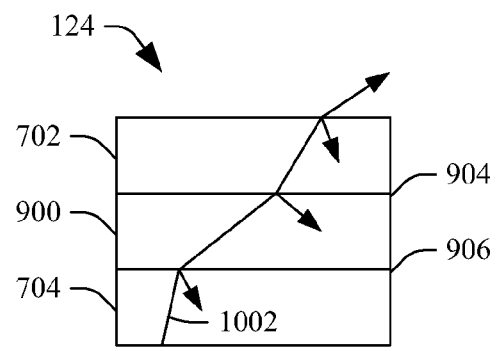
FIG. 10 illustrates a variation of the display region of FIG. 8 with the optical bond omitted therefrom.

FIGS. 9 and 10 show embodiments in which the optical coupling 706 is omitted. In this embodiment, air 900 is located between the cover lens 702 and the screen 704. As shown, external light 902 refracts at the cover lens 702/air 900 interface 904 and off the air 900/the screen 704 interface 906.

Likewise, emitted light 1002 refracts at the screen 704/air 900 interface 906 and at the air 900/the cover lens interface 904.

Figure 11:
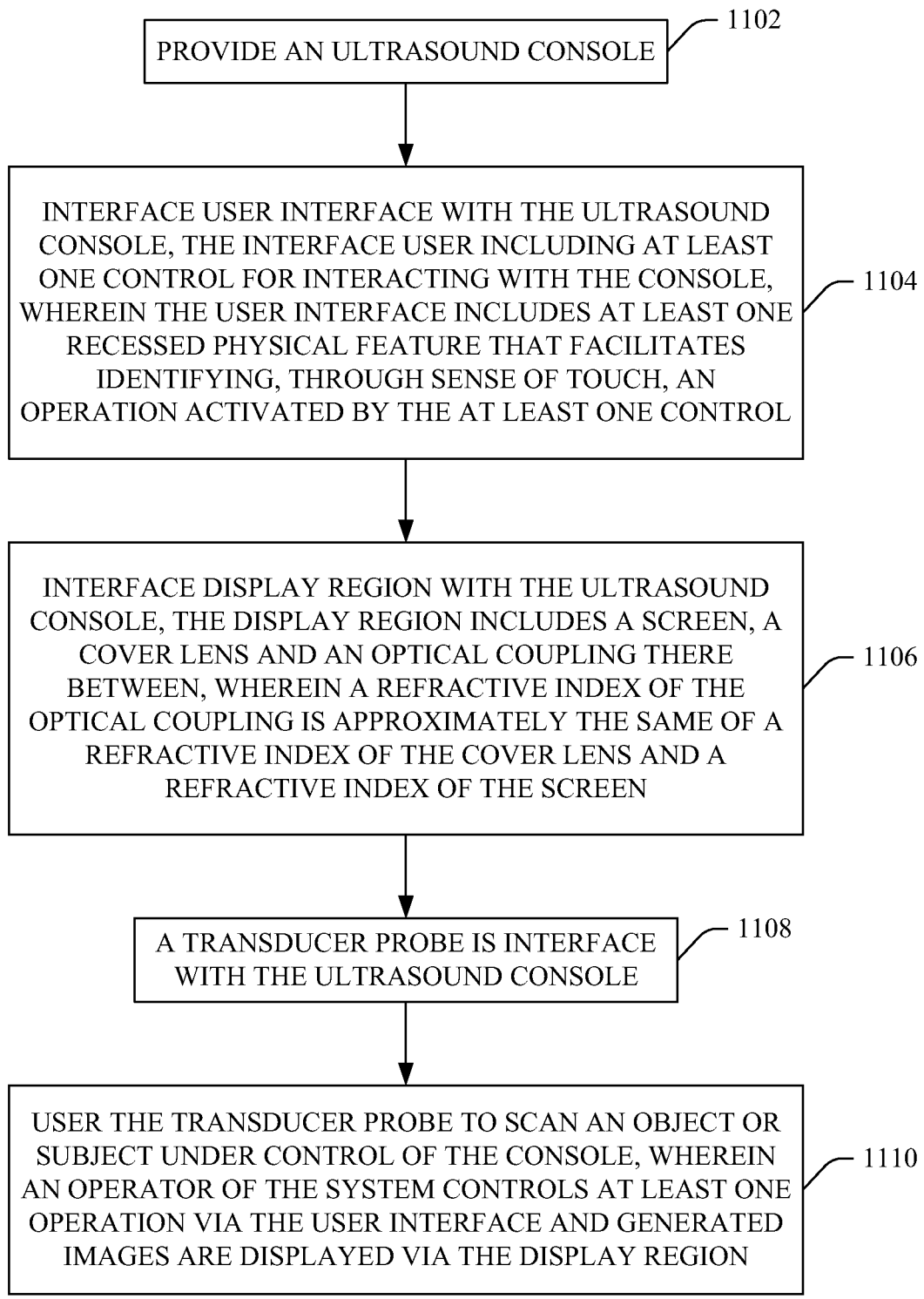
FIG. 11 illustrates an example method in accordance with the embodiments disclosed herein.

FIG. 11 illustrates a method in accordance with the embodiments disclosed herein.

It is to be appreciated that the order of the following acts is provided for explanatory purposes and is not limiting. As such, one or more of the following acts may occur in a different order. Furthermore, one or more of the following acts may be omitted and/or one or more additional acts may be added.

At 1102, an ultrasound console is provided.

At 1104, a user interface is interfaced with the ultrasound console. As discussed herein, the user interface includes at least one control for interacting with the console, wherein the user interface includes at least one recessed physical feature that facilitates identifying, through sense of touch, an operation activated by the at least one control.

At 1106, a display region is interfaced with the ultrasound console. As discussed herein, the display region includes a screen, a cover lens and an optical coupling there between, wherein a refractive index of the optical coupling is approximately the same of a refractive index of the cover lens and a refractive index of the screen.

At 1108, a transducer probe is interfaced with the ultrasound console.

At 1110, the transducer probe is used to scan an object or subject under control of the console, wherein an operator of the system controls at least one operation via the user interface and generated images are displayed via the display region.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. An ultrasound imaging system, comprising:
   a probe, including: a transducer array with at least one transducer element that transmits ultrasound signal and receives echo signals produced in response thereto;
   a console, including: a controller that controls the at least one element to transmit the ultrasound signals and receive the echo signals, and an echo processor that processes the received echoes and generates images indicative thereof; and
   a user interface, including a flat touchscreen panel having a planar surface, wherein the flat touchscreen panel is an active touch sensitive area, the active touch sensitive area includes at least two predetermined regions, each of the at least two predetermined regions includes at least one control for interacting with the console, wherein each control is in a recess in the planar surface, and the planar surface, the recess, and the control in the recess contain a same touchscreen material, each of the at least one control controls a different operation of the ultrasound imaging system in response to being actuated by a gesture, and each of the at least two predetermined regions includes at least one recessed physical feature in the planar surface that facilitates identifying, through sense of touch, an operation activated by the at least one control, wherein the flat touchscreen panel is not a frame of a display monitor.

2. The ultrasound imaging system of claim 1, wherein the flat touchscreen panel is one of a liquid crystal display (LCD), a thin film transistor liquid crystal display (TFT LCD), or an organic light-emitting diode (OLED) display.

3. The ultrasound imaging system of claim 2, wherein the user interface includes a cover lens optically bonded to an entirety of the flat touchscreen panel.

4. The ultrasound imaging system of claim 1, wherein a predetermined region of the at least two predetermined regions comprises:
 a transition from the planar surface into the flat touchscreen panel, forming the recess; and
 a first flat recess surface within the recess;
 wherein the at least one recessed physical feature includes the transition and the first flat recess surface.

5. The ultrasound imaging system of claim 4, wherein the first flat recess surface actuates the at least one control.

6. The ultrasound imaging system of claim 5, wherein the at least one control includes a touch pad area.

7. The ultrasound imaging system of claim 1, wherein the at least one recessed physical feature includes a first recess with a first flat recess surface and a second recess with a second flat recess surface, and the flat touchscreen panel, further comprising:
 a first transition from the planar surface into the flat touchscreen panel to the first flat recess surface, forming the first recess;
 a second transition from the first flat recess surface into the flat touchscreen panel to the second flat recess surface, forming the second recess,
 wherein the at least one recessed physical feature includes the first transition, the first flat recess surface, the second transition, and the second flat recess surface.

8. The ultrasound imaging system of claim 7, wherein the second flat recess surface actuates the at least one control.

9. The ultrasound imaging system of claim 8, wherein the at least one control includes a push button.

10. The ultrasound imaging system of claim 1, wherein the at least one recessed physical feature includes a first recess with a first flat recess surface and a protrusion and a second recess with a second flat recess surface, and the flat touchscreen panel, further comprising:
 a first transition from the planar surface into the flat touchscreen panel to the first flat recess surface, forming the first recess, wherein the protrusion is spaced apart from the first transition by a non-zero distance;
 a second transition from the first flat recess surface into the flat touchscreen panel to the second flat recess surface, forming the second recess,
 wherein the at least one recessed physical feature includes at least two recessed physical features, a first of the at least two recessed physical features including the first transition, the first flat recess surface and the protrusion, and a second of the at least two recessed physical features including the second transition and the second flat recess surface.

11. The ultrasound imaging system of claim 10, wherein the at least one control includes at least a first control and a second control, wherein the first flat recess surface actuates the first control and the second flat recess surface actuates the second control.

12. The ultrasound imaging system of claim 11, wherein first control includes a rotary control and the second control includes a push button control.

13. The ultrasound imaging system of claim 1, further comprising:
 a display region, including: a screen, a cover lens and an optical coupling there between, wherein a refractive index of the optical coupling is approximately the same of a refractive index of the cover lens and a refractive index of the screen.

14. The ultrasound imaging system of claim 1, wherein the flat touchscreen panel further comprises a bottom, the planar surface is a first distance away from the bottom surface, the recess is a second distance away from the bottom surface, and the first distance is greater than the second distance.

15. The ultrasound imaging system of claim 1, wherein the planar surface, the transition and the recess are all part of a same surface.

16. The ultrasound imaging system of claim 1, wherein the planar surface has a first thickness, the recess has a second thickness, and the first thickness is greater than the second thickness.

17. A method, comprising:
 providing an ultrasound console;
 interfacing a user interface with the ultrasound console, wherein the user interface includes a planar active touch sensitive area with a transition into a recess in the planar active touch sensitive area, wherein the recess is a control configured to control a sensitive area, the transition to the recess, the recess and the control contain a same touch screen material, none of the planar active touch sensitive area, the transition to the recess, the recess or the control is a frame of a display monitor, and the transition provides a recessed physical feature;
 interfacing a display region with the ultrasound console, wherein the display region includes a screen, a cover lens and an optical coupling there between, wherein a refractive index of the optical coupling is approximately the same of a refractive index of the cover lens and a refractive index of the screen;
 interfacing a transducer probe with the ultrasound console; and
 using the transducer probe to scan an object or subject under control of the console, wherein an operator of the system controls at least one operation via the user interface and generated images are displayed via the display region.

18. The method of claim 17, further comprising:
 identifying a type of the control by the recessed physical feature.

19. The method of claim 18, where the control is one of a touch pad, a rotary control and a push button.

20. The method of claim 19, further comprising:
 actuating the control with a touch gesture on a surface of the control.

* * * * *